(12) United States Patent
Walter

(10) Patent No.: US 8,177,900 B2
(45) Date of Patent: May 15, 2012

(54) COMPOSITIONS FOR USE IN MAKING MODELS

(75) Inventor: Jose Walter, Ranson, WV (US)

(73) Assignee: Cbite, Inc., Chantilly, VA (US)

( * ) Notice: Subject to any disclaimer, the term of this patent is extended or adjusted under 35 U.S.C. 154(b) by 1075 days.

(21) Appl. No.: 11/808,988

(22) Filed: Jun. 14, 2007

(65) Prior Publication Data

US 2007/0241472 A1 Oct. 18, 2007

Related U.S. Application Data

(63) Continuation-in-part of application No. 10/795,457, filed on Mar. 9, 2004, now abandoned, which is a continuation-in-part of application No. 10/232,656, filed on Sep. 3, 2002, now abandoned.

(51) Int. Cl.
| | |
|---|---|
| C09K 3/00 | (2006.01) |
| B28B 7/36 | (2006.01) |
| B28B 7/28 | (2006.01) |
| B28B 7/34 | (2006.01) |
| A61C 13/00 | (2006.01) |
| A61C 13/08 | (2006.01) |

(52) U.S. Cl. ........ 106/38.35; 106/35; 106/38.2; 264/16; 264/19; 433/202.1

(58) Field of Classification Search .................... 106/35, 106/38.35, 638, 38.2; 264/16, 19, 669; 206/17.4; 433/202.1; 523/109
See application file for complete search history.

(56) References Cited

U.S. PATENT DOCUMENTS

| | | | | |
|---|---|---|---|---|
| 3,620,778 | A * | 11/1971 | Morrell | 523/109 |
| 4,409,347 | A * | 10/1983 | Rottmaier et al. | 524/91 |
| 4,443,574 | A * | 4/1984 | Coq et al. | 524/423 |
| 4,585,417 | A * | 4/1986 | Sozio et al. | 433/202.1 |
| 4,746,365 | A * | 5/1988 | Babcock et al. | 524/4 |
| 4,768,951 | A * | 9/1988 | Abiru et al. | 433/48 |
| 5,120,778 | A * | 6/1992 | Price et al. | 524/94 |
| 5,221,342 | A * | 6/1993 | Minami et al. | 106/461 |
| 5,698,610 | A * | 12/1997 | Futami et al. | 523/109 |
| 5,718,749 | A * | 2/1998 | Horiuchi et al. | 106/38.35 |

FOREIGN PATENT DOCUMENTS

GB 2 264 114 * 8/1993

* cited by examiner

*Primary Examiner* — Anthony J Green
*Assistant Examiner* — Pegah Parvini
(74) *Attorney, Agent, or Firm* — Glenna Hendricks

(57) ABSTRACT

Gypsum-based molding materials are customized by hydrating the molding material to workable (malleable) consistency with a moistening solution containing 0.001 to 60% polytetrafluoroethylene. The addition of latex results in a more flowable material.

7 Claims, No Drawings

COMPOSITIONS FOR USE IN MAKING MODELS

This application is a continuation-in-part of U.S. patent application Ser. No. 10/795,457 filed Mar. 9, 2004, now abandoned, which is a continuation-in-part of U.S. patent application Ser. No. 10/232,656 filed Sep. 3, 2002, now abandoned.

FIELD AND BACKGROUND OF THE INVENTION

This invention relates to compositions for use in making dental models and other molded or shaped objects. The invention provides novel liquid formulations for moistening gypsum-containing materials. The use of the liquids in the manner described herein imparts strength of the molded or sculpted objects resulting from practice of the new methods disclosed herein. The use of the new formulations for moistening stone used in forming models has been found to be particularly advantageous for dental laboratory practices.

In making models for restoration and replacement in dentistry, it is important that the molding materials used be both readily workable and of sufficient strength to provide models that are sharp and do not crumble. It is sometimes necessary to stock various types of materials of varying strength and hardening properties in order to have materials that are optimum for the particular purpose for which the models are made. This presents serious disadvantages for dental laboratories where small amounts of material are used.

Models are created using a negative impression of the object of interest. The negative impression is then filled with a casting material which hardens, thus creating a model of the object to be made or modified. In order to work with these models, the casting material must sometimes be sawed into smaller pieces. It is essential to be able to realign the pieces in the appropriate manner and to have materials which hold their shape without crumbling, but which can be worked on and reassembled.

SUMMARY OF THE INVENTION

It is the purpose of this invention to provide materials for making customized molding material for use in making models. A particularly advantageous aspect of the invention is provision of kits with hydrating liquids which impart varying hardness to final products for use in making models. Gypsum-based molding materials are customized by hydrating the molding material to workable (malleable) consistency with a moistening solutions containing 0.001 to 35% polytetrafluoroethylene (PTFE). When the product obtained from Dupont is used as sold for moistening agent, the amount of PTFE is about 60%. While such use is acceptable, sufficient hardness for use in dental models was obtained with ≦35% PTFE in the moistening agent. Other materials which increase other desired properties such as latexes, which increase flowability, or materials such as dyes which impart color to the final product may be used in the practice of the invention.

DETAILED DESCRIPTION OF THE INVENTION

It has now been found that addition of varying amounts of polytetrafluoroethylene (PTFE) to liquids used for moistening molding materials for making models such as that used in making dental models, especially those containing calcium sulfate (gypsum), will increase strength and sharpness of the models. The gypsum-containing material as used in dentistry is often called "stone". The amount of PTFE used in a particular moistening liquid depends on the workability and strength required. When greater amounts of PTFE are used, the material may be harder to work, but will be less likely to crumble. While the materials described herein were developed for purposes of making dental models, the PTFE/gypsum-based molding material produced using the moistening liquids may be used for making any models such as those used in manufacturing of parts or packaging. Such applications have wide use in industries such as aerospace, automotive, laboratory and medical equipment industries and in the building industry. The preparation of casting materials for use in making decorative objects is also an aspect of the invention. Such objects may be molded or carved, depending on the work at hand and the preferences of the artisan.

Example 1

Compositions containing 58%-62% PTFE (identified below as "Dupont PTFE product") manufactured by Dupont were used in making the following compositions:

| Formulation | % Dupont PTFE product | % water |
|---|---|---|
| 1 | 0.1% | 99.9% |
| 2 | 0.2% | 99.8% |
| 3 | 0.8% | 99.2% |
| 4 | 8.34% | 91.66% |
| 5 | 16.67% | 83.33% |
| 6 | 33.34% | 66.66% |
| 7 | 100.00% | none |

To each gallon of formulation, 2 drops of dye (a different color for each formulation) were added so that the materials containing the PTFE could be identified. Formulations 1-3, when used to hydrate gypsum-based molding material in place of water usually used for hydration for making dental models produced a resin-like material upon drying. Hydration of stone using formulations 4-6 resulted in epoxy-like materials. The epoxy-like models were very smooth and hard when dried, but could be cut with appropriate saws to provide very strong models of the teeth. The formulations 1, 2 and 3 contain about 0.05% to 0.5% PTFE. Formulations 4, 5, 6 and 7 contain about 9% to about 60% of the PTFE.

While the instant invention was developed originally for making models of teeth, it may be used in other applications such as making models of parts for making reverse models of openings in materials for which fittings are required to maintain shape.

Example 2

The following formulations were formulated made using a dye which is sold for use in coloring foods:

| Formulations | % Dupont TEFLON T-30 ™ | % water | drops dye/gallon |
|---|---|---|---|
| 1 | 0.1 | 99.9 | 2 |
| 2 | 02 | 99.8 | 2 |
| 3 | 0.8 | 99.2 | 2 |
| 4 | 8.34 | 91.66 | 2 |
| 5 | 10.67 | 83.33 | 2 |
| 6 | 33.34 | 66.66 | 2 |

In all instances, the use of the resulting liquid formulations as moistening agent for the gypsum-containing material resulted in molding materials which were colored throughout. The hardness of the final product depended on the amount of TEFLON™ in the moistening agent. The dye chosen in any particular instance would depend on the properties of the dye as required for the particular work. In the instant case, food dye was used for its non-toxic properties and availability. If the materials are to be used for crafts, avoidance of toxicity would be of paramount importance. For use in decorative items, durability of color may be of greater importance. For decorative objects, the production of products of consistent color throughout the molded object that would render a final product in which chips would be less noticeable would be an important goal.

Example 3

It has, furthermore, been found that addition of a latex to the moistening material results in a product that flows more easily. PLEXTOL™ B 500 (Cas No. 1336-21-6) and 510 D were obtained from Polymer Latex GmbH & Co. KG of Germany. When using this latex product and similar products (i.e., products having moistening liquid to achieve desirable flow properties. The following hydrating compositions were prepared:

| Forulation | TEFLON T-30 ™ | PLEXTOL ™ | water |
|---|---|---|---|
| 1 | 1 ounce | None | 127 ounces |
| 2 | 2.56 ounces | 144 drops (510 D) | 125.19 ounces |
| 3 | 19.2 ounces | 64 drops (500 B) | 108 ounces |
| 4 | 20.8 ounces | 112 drops (500 B) | 107.05 ounces |
| 5 | 27.2 ounces | 112 drops (500 B) | 100.65 ounces |

A drop equals about .05 ml

The compositions are listed in order from those imparting to the final stone/hydrating liquid molding product the least hardness to greatest hardness. The last three compositions were quite hard and especially unlikely to crumble when cut. The workman must consider malleability vs. hardness when choosing the particular moistening agent. The harder materials are quite particularly useful for making building materials (for making objects such as cornices). The harder materials are also sometimes more appropriate for making decorative objects or for sculpting.

The choice of the particular latex chosen will also depend on the type of properties desired in the end product. For example, a latex which quickly forms a strong, hard coating is less useful for purposes of making a product in instances where malleability is an essential property.

When used to make models, no polymerization step is needed. While there are many means of polymerization, in the small dental laboratories or craft shop, heating would provide the most likely means used for polymerization. The fact that such a step is not required decreases cost and increases efficiency, since simply moistening the gypsum containing material with a moistening material containing the desired amount of PTFE will, upon hardening, provide the desired hardness to the models formed when the novel moistening liquids are used in accord with the teachings herein.

Example 4

A composition of example 1, the formula identified as formula 2, was used as the hydrating liquid. After the gypsum-containing casting material was moistened with the product identified as formula 2 in example 1, a negative impression was filled with the casting material of formula 2 to create a model of a patient's teeth. Once the casting material had hardened sufficiently, the trays and supports with the casting material were removed from the impression and allowed to harden more fully. When the casting material had fully hardened, the tray with the models were removed from the tray support.

Example 5

The process of example 4 was followed using the hydrating liquids of example 3. The models made from materials wherein the formulations of example 3 where used as moistening agents were compared for workability and hardness. The product made with formulation 5 as most unlikely to crumble, but was also harder to sculpt. However, all of the liquid moistening formulations were useful for purposes of preparing materials for making models of teeth.

Compositions of the invention may be used in making many objects, including decorative items produced in molds, sculpted or worked with tools commonly used in carpentry, etc. Products such as decorative cornices and pillars are useful for building. While use of dyes in compositions have been exemplified using water-soluble food coloring, other means of coloring such as oil and alcohol soluble coloring agents may be used. Furthermore, for use in making decorative items, small amounts of agents to add interest to the final product such as small colored particles, including finely ground bits of resin or glass, may be incorporated in compositions for use in producing decorative items.

What I claim is:

1. A method of producing, without heating, customized hardening molding materials consisting of the steps of:
    (a) preparing an aqueous moistening liquid consisting of 0.001 to 60% polytetrafluoroethylene in aqueous liquid, and
    (b) then moistening dry gypsum molding material with the liquid preparation prepared in step (a).

2. The method of claim 1 wherein the moistening liquid prepared in step (a) consists of 0.05% to 5% polytetrafluoroethylene.

3. The method of claim 1 wherein the moistening liquid prepared in step (a) consists of 9% to 20% polytetrafluoroethylene.

4. A method of producing, without a polymerization step, customized hardening molding materials consisting of the steps of:
    (a) preparing an aqueous moistening liquid formulation consisting of from 0.001 to 35% polytetrafluoroethylene and latex in aqueous liquid,
    (b) then moistening dry gypsum molding material with the liquid formulation prepared in step (a).

5. The method of claim 4 wherein the moistening liquid prepared in step (a) consists of 0.05% to 5% polytetrafluoroethylene.

6. The method of claim 4 wherein the moistening liquid prepared in step (a) consists of 9% to 20% polytetxafluoroethylene.

7. A method of producing, without a polymerization step, customized hardening molding materials consisting of the steps of:
    (a) preparing an aqueous moistening liquid formulation consisting of from 9 to 20% polytetrafluoroethylene in aqueous liquid and
    (b) then moistening dry gypsum containing molding material with the liquid formulation prepared in step (a).

* * * * *